(12) United States Patent
Sankaran et al.

(10) Patent No.: US 8,617,820 B2
(45) Date of Patent: Dec. 31, 2013

(54) USE OF GLYCOSAMINOGLYCANS TO REDUCE NON-SPECIFIC BINDING IN IMMUNOASSAYS

(75) Inventors: Banumathi Sankaran, Pittsford, NY (US); Sheryl S. Sullivan, Hilton, NY (US); Darrell C. Haynes, Rochester, NY (US); Philip C. Hosimer, Rochester, NY (US); Graham Yearwood, Bethlehem, PA (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 700 days.

(21) Appl. No.: 11/846,390

(22) Filed: Aug. 28, 2007

(65) Prior Publication Data

US 2009/0061455 A1 Mar. 5, 2009

(51) Int. Cl.
*C12Q 1/00* (2006.01)
*G01N 33/00* (2006.01)
*G01N 33/53* (2006.01)
*C12N 5/07* (2010.01)

(52) U.S. Cl.
USPC .............. 435/7.1; 435/4; 435/7.25; 435/7.92; 435/327; 435/344.1; 436/174; 436/503; 436/507

(58) Field of Classification Search
None
See application file for complete search history.

(56) References Cited

U.S. PATENT DOCUMENTS

| | | | |
|---|---|---|---|
| 5,529,985 A * | 6/1996 | Petitou et al. ................ | 514/53 |
| 5,616,460 A | 4/1997 | Figard | |
| 5,710,006 A | 1/1998 | Kiaei et al. | |
| 5,891,647 A * | 4/1999 | Lormeau et al. ............... | 435/7.2 |
| 5,922,690 A * | 7/1999 | Van Gorp et al. ............... | 514/54 |
| 6,376,206 B1 | 4/2002 | Katus et al. | |
| 6,627,404 B1 | 9/2003 | Buechler et al. | |
| 6,887,474 B1 * | 5/2005 | Stewart et al. ............ | 424/178.1 |
| 2005/0164317 A1 | 7/2005 | Buechler et al. | |
| 2006/0105472 A1 | 5/2006 | Teng et al. | |

FOREIGN PATENT DOCUMENTS

| | | |
|---|---|---|
| JP | 2238361 A | 9/1990 |
| JP | 8029420 A | 2/1996 |
| JP | 2002340899 A | 11/2002 |
| WO | WO 92/21769 A1 | 12/1992 |
| WO | 96/10076 A1 | 4/1996 |
| WO | WO 2004/092733 A1 | 10/2004 |

OTHER PUBLICATIONS

Speth et al., (Clinical Biochemistry. 2002. vol. 35: 355-362).*
Hong et al., (International Immunopharmacology. 2005. vol. 5:381-391).*
Cardinale et al., (Ann. Oncol. 2002. May. vol. 13(5):710-715).*

(Continued)

*Primary Examiner* — Ja'na Hines
(74) *Attorney, Agent, or Firm* — Susan J. Timian

(57) ABSTRACT

An immunoassay reagent is provided which comprises an analyte binding agent in a diluent, and a glycosaminoglycan in an amount sufficient to reduce non-specific binding in an assay of a sample for the analyte. Provided is such an immunoassay reagent in which the analyte is troponin I, the analyte binding agent is a biotinylated anti-troponin I antibody, and the glycosaminoglycan is chondroitin sulfate. A sample composition is also provided which comprises a sample to be assayed for the presence of an analyte, an analyte binding agent, and a glycosaminoglycan other than heparin. Further provided is a method of detecting an analyte in a sample, in which non-specific binding is reduced in the method using a glycosaminoglycan.

8 Claims, 4 Drawing Sheets

| | NEAT | Cond #1 | Cond #2 | Cond #3 | Cond #4 | Cond #5 | Cond #6 | Cond #7 | Cond #8 |
|---|---|---|---|---|---|---|---|---|---|
| | | N-Acetyl-Glucosamine | N-Acetyl-Galactosamine | Glucosamine | N-Acetylneuraminic Acid | Chondroitin Sulfate C | Chitin | Mucin | Mannose |
| | Pred. Conc. | Pred. Conc. | Pred. Conc. | Pred. Conc. | Pred. Conc. | Pred. Conc. | Pred. Conc. | Pred. Conc. | Pred. Conc. |
| NEG POOL | 0.00 | 0.00 | 0.00 | 0.00 | 0.00 | 0.00 | 0.00 | 0.00 | 0.00 |
| NEG POOL | 0.00 | 0.00 | 0.00 | 0.00 | 0.00 | 0.00 | 0.00 | 0.00 | 0.00 |
| POS POOL | 4.63 | 4.18 | 4.08 | 3.96 | 3.70 | 3.54 | 3.61 | 3.57 | 3.58 |
| POS POOL | 4.64 | 4.19 | 3.94 | 3.99 | 3.67 | 3.55 | 3.67 | 3.60 | 3.61 |
| TC0005 | 0.52 | 0.48 | 0.45 | 0.44 | 0.45 | 0.01 | 0.44 | 0.44 | 0.46 |
| TC0005 | 0.58 | 0.54 | 0.45 | 0.48 | 0.40 | 0.02 | 0.40 | 0.37 | 0.44 |
| 56413 | 0.80 | 0.48 | 0.63 | 0.58 | 0.62 | 0.00 | 0.68 | 0.47 | 0.56 |
| 56413 | 0.83 | 0.62 | 0.62 | 0.60 | 0.61 | 0.00 | 0.64 | 0.47 | 0.56 |
| 58732 | 5.49 | 4.67 | 4.93 | 4.50 | 4.96 | 0.11 | 5.08 | 4.75 | 4.91 |
| 58732 | 4.64 | 4.98 | 4.07 | 4.20 | 4.50 | 0.10 | 4.51 | 4.37 | 4.16 |
| 58201 | 1.95 | 1.83 | 1.76 | 1.76 | 2.20 | 0.00 | 2.23 | 1.86 | 1.87 |
| 58201 | 2.01 | 2.19 | 2.05 | 1.95 | 2.09 | 0.00 | 1.87 | 1.98 | 1.63 |
| 5654 | 0.88 | 0.76 | 0.80 | 0.85 | 0.90 | 0.20 | 1.00 | 0.41 | 0.93 |
| 5654 | 0.88 | 1.01 | 0.81 | 0.84 | 0.82 | 0.20 | 0.83 | 0.43 | 0.85 |
| 5345 | 1.08 | 1.02 | 0.98 | 0.91 | 1.09 | 0.08 | 0.97 | 0.70 | 1.01 |
| 5345 | 1.10 | 1.10 | 0.96 | 1.00 | 0.91 | 0.08 | 0.96 | 0.50 | 0.92 |
| 52674 | 1.19 | 1.04 | 1.13 | 1.07 | 1.15 | 0.00 | 1.20 | 0.64 | 1.19 |
| 52674 | 1.11 | 1.49 | 1.03 | 0.98 | 0.99 | 0.01 | 1.13 | 0.64 | 1.12 |
| 5686 | 1.10 | 1.11 | 1.15 | 1.06 | 1.07 | 0.00 | 1.14 | 0.60 | 1.24 |
| 5686 | 1.18 | 1.24 | 1.13 | 1.08 | 1.02 | 0.00 | 1.23 | 0.63 | 1.06 |

(56) References Cited

OTHER PUBLICATIONS

Bjerner, Johan, et al., "Immunometric Assay Interference: Incidence and Prevention", Clin Chem 48(4):613-621 (2002).

Eriksson, Susann, et al., "Negative Interference in Cardiac Troponin I Immunoassays from a Frequently Occurring Serum and Plasma Component", Clin Chem 49(7):1095-1104 (2003).

Hawkins, Robert C., "Hemolysis Interference in the Ortho-Clinical Diagnostics Vitros ECi cTnI Assay", Clin Chem 49(7):1226-1227 (2003).

Kim, Wesley J., et al., "Performance of a Revised Cardiac Troponin Method That Minimizes Interferences from Heterophilic Antibodies", Clin Chem 48(7):1028-1034 (2002).

Lin, Chien-Tsai, et al., "Positive Interference from Contrast Media in Cardiac Troponin I Immunoassays", Kaohsiung J Med Sci 22(3):107-113 (2006).

Pereira, H. Anne, et al., "Quantitation of a cationic antimicrobial granule protein of human polymorphonuclear leukocytes by ELISA", J Immunol Methods 117:115-120 (1989).

Roberts, William L., et al., "Prevention of Analytical False-Positive Increases of Cardiac Troponin I on the Stratus II Analyzer", Clin Chem 43(5):860-861 (1997).

Stiegler, Hugo, et al., "Lower Cardiac Troponin T and I Results in Heparin-Plasma Than in Serum", Clin Chem 46(9):1338-1344 (2000).

Valimaa, Lasse, and Laurikainen, Katja, "Comparison study of streptavidin-coated microtitration plates", J Immunol Methods 308:203-215 (2006).

Waterboer, Tim, et al., "Suppression of non-specific binding in serological Luminex assays", J Immunol Methods 309:200-204 (2006).

Yeo, Kiang-Teck J., et al., "Performance of the enhanced Abbott AxSYM Cardiac Troponin I reagent in patients with heterophilic antibodies", Clin Chim Acta 292:13-23 (2000).

Lam, Nicole Y. L. et al., "EDTA Is a Better Anticoagulant than Heparin or Citrate for Delayed Blood Processing for Plasma DNA Analysis", Clinical Chemistry 50(1): 256-257 (2004).

* cited by examiner

Fig. 1

|  | NEAT | Cond #1 | Cond #2 | Cond #3 | Cond #4 | Cond #5 | Cond #6 | Cond #7 | Cond #8 |
|---|---|---|---|---|---|---|---|---|---|
|  |  | N-Acetyl-Glucosamine | N-Acetyl-Galactosamine | Glucosamine | N-Acetylneuraminic Acid | Chondroitin Sulfate C | Chitin | Mucin | Mannose |
|  | Pred. Conc. | Pred. Conc. | Pred. Conc. | Pred. Conc. | Pred. Conc. | Pred. Conc. | Pred. Conc. | Pred. Conc. | Pred. Conc. |
| NEG POOL | 0.00 | 0.00 | 0.00 | 0.00 | 0.00 | 0.00 | 0.00 | 0.00 | 0.00 |
| NEG POOL | 0.00 | 0.00 | 0.00 | 0.00 | 0.00 | 0.00 | 0.00 | 0.00 | 0.00 |
| POS POOL | 4.63 | 4.18 | 4.08 | 3.96 | 3.70 | 3.54 | 3.61 | 3.57 | 3.58 |
| POS POOL | 4.64 | 4.19 | 3.94 | 3.99 | 3.67 | 3.55 | 3.67 | 3.60 | 3.61 |
| TC0005 | 0.52 | 0.48 | 0.45 | 0.44 | 0.45 | 0.01 | 0.44 | 0.44 | 0.46 |
| TC0005 | 0.58 | 0.54 | 0.45 | 0.48 | 0.40 | 0.02 | 0.40 | 0.37 | 0.44 |
| 58413 | 0.80 | 0.48 | 0.63 | 0.58 | 0.62 | 0.00 | 0.68 | 0.47 | 0.56 |
| 58413 | 0.83 | 0.62 | 0.62 | 0.60 | 0.61 | 0.00 | 0.64 | 0.47 | 0.56 |
| 58732 | 5.49 | 4.67 | 4.93 | 4.50 | 4.96 | 0.11 | 5.08 | 4.76 | 4.91 |
| 58732 | 4.64 | 4.98 | 4.07 | 4.20 | 4.50 | 0.10 | 4.51 | 4.37 | 4.16 |
| 58201 | 1.95 | 1.83 | 1.76 | 1.76 | 2.20 | 0.00 | 2.23 | 1.86 | 1.87 |
| 58201 | 2.01 | 2.19 | 2.05 | 1.95 | 2.09 | 0.00 | 1.87 | 1.98 | 1.63 |
| 5654 | 0.88 | 0.76 | 0.80 | 0.85 | 0.90 | 0.20 | 1.00 | 0.41 | 0.93 |
| 5654 | 0.88 | 1.01 | 0.81 | 0.84 | 0.82 | 0.20 | 0.83 | 0.43 | 0.85 |
| 5345 | 1.08 | 1.02 | 0.98 | 0.91 | 1.09 | 0.08 | 0.97 | 0.70 | 1.01 |
| 5345 | 1.10 | 1.10 | 0.96 | 1.00 | 0.91 | 0.08 | 0.96 | 0.50 | 0.92 |
| 52674 | 1.19 | 1.04 | 1.13 | 1.07 | 1.15 | 0.00 | 1.20 | 0.64 | 1.19 |
| 52674 | 1.11 | 1.49 | 1.03 | 0.98 | 0.99 | 0.01 | 1.13 | 0.64 | 1.12 |
| 5686 | 1.10 | 1.11 | 1.15 | 1.06 | 1.07 | 0.00 | 1.14 | 0.60 | 1.24 |
| 5686 | 1.18 | 1.24 | 1.13 | 1.08 | 1.02 | 0.00 | 1.23 | 0.63 | 1.06 |

Fig. 2

|  | Condition 1 | | Condition 2 | | Condition 3 | | Condition 4 | | Condition 5 | | Condition 6 | | Condition 7 | |
|---|---|---|---|---|---|---|---|---|---|---|---|---|---|---|
|  | ALU | Trpt (ng/mL) | ALU | Trpt (ng/mL) | ALU | Trpt (ng/mL) | ALU | Trpt (ng/mL) | ALU | Trpt (ng/mL) | ALU | Trpt (ng/mL) | ALU | Trpt (ng/mL) |
| MAS1 | 29.15 | 0.52 | 29.39 | 0.57 | 23.80 | 0.59 | 27.25 | 0.51 | 27.82 | 0.55 | 20.83 | 0.57 | 29.67 | 0.52 |
| MAS2 | 1109.00 | 7.28 | 1066.22 | 7.71 | 986.41 | 8.08 | 1087.37 | 7.44 | 1050.92 | 7.34 | 922.34 | 7.84 | 1182.84 | 7.31 |
| MAS3 | 1938.47 | 11.17 | 1938.47 | 12.16 | 1182.84 | 9.29 | 1947.08 | 11.66 | 1852.02 | 11.38 | 1639.57 | 12.34 | 2037.61 | 11.10 |
| Neg pool | 1.52 | 0.00 | 1.21 | 0.00 | 1.47 | 0.00 | 1.44 | 0.00 | 1.53 | 0.00 | 1.32 | 0.00 | 1.70 | 0.00 |
| Pos pool | 362.24 | 3.13 | 364.95 | 3.33 | 348.08 | 3.68 | 382.54 | 3.37 | 391.03 | 3.47 | 350.50 | 3.80 | 352.60 | 2.95 |
| TC0005 | 4.68 | 0.11 | 4.14 | 0.12 | 4.08 | 0.13 | 3.20 | 0.07 | 3.12 | 0.07 | 2.82 | 0.06 | 8.74 | 0.21 |
| 59413 | 1.95 | 0.02 | 2.01 | 0.03 | 1.92 | 0.02 | 2.23 | 0.03 | 1.89 | 0.02 | 1.66 | -0.02 | 10.68 | 0.25 |
| 58732 | 8.72 | 0.21 | 5.91 | 0.18 | 4.38 | 0.15 | 12.07 | 0.29 | 8.36 | 0.23 | 6.67 | 0.24 | 163.28 | 1.68 |
| 58201 | 1.74 | 0.01 | 1.50 | 0.00 | 1.66 | 0.00 | 1.72 | 0.00 | 1.57 | 0.00 | 1.55 | -0.03 | 57.39 | 0.81 |
| 5664 | 13.07 | 0.29 | 8.21 | 0.24 | 5.31 | 0.19 | 26.73 | 0.50 | 24.11 | 0.50 | 10.60 | 0.36 | 57.62 | 0.81 |
| 5345 | 7.14 | 0.17 | 6.43 | 0.19 | 4.74 | 0.16 | 7.10 | 0.18 | 7.03 | 0.20 | 5.51 | 0.19 | 66.40 | 0.89 |
| 5686 | 4.71 | 0.11 | 5.34 | 0.16 | 2.95 | 0.08 | 2.79 | 0.05 | 3.10 | 0.07 | 2.75 | 0.06 | 49.65 | 0.73 |
| 52574 | 3.80 | 0.08 | 4.42 | 0.13 | 3.25 | 0.10 | 4.12 | 0.10 | 4.07 | 0.11 | 3.69 | 0.11 | 24.74 | 0.46 |
| CS | 1mg/mL | | 2mg/mL | | 4mg/mL | | 1mg/mL | | 2mg/mL | | 4mg/mL | | 0mg/mL | |
| EDTA | - | | - | | - | | + | | + | | + | | - | |

| CONC. | | | | Kit Lot |
|---|---|---|---|---|
| | CS-A | CS-B | CS-C | PredConc |
| 7003 | 0.002 | 0.002 | 0.004 | 0.000 |
| 7009 | 0.005 | 0.005 | 0.004 | 0.338 |
| 7011 | 0.005 | 0.003 | 0.005 | 0.000 |
| 7015 | 0.012 | 0.011 | 0.010 | 0.000 |
| 7027 | 0.007 | 0.006 | 0.008 | 0.002 |
| 7029 | 0.006 | 0.004 | 0.005 | 0.095 |
| 7036 | 0.006 | 0.007 | 0.005 | 0.000 |
| 7041 | 0.005 | 0.005 | 0.004 | 0.000 |
| 7047 | 0.005 | 0.006 | 0.005 | 0.004 |
| 7063 | 0.004 | 0.005 | 0.004 | 0.704 |
| 7065 | 0.026 | 0.024 | 0.024 | 0.113 |
| 7066 | 0.005 | 0.004 | 0.005 | 0.177 |
| 7076 | 0.013 | 0.012 | 0.014 | 0.117 |
| 7084 | 0.007 | 0.005 | 0.006 | 0.383 |
| 7086 | 0.006 | 0.005 | 0.004 | 0.083 |
| 7115 | 0.036 | 0.036 | 0.032 | 0.175 |
| 7116 | 0.010 | 0.008 | 0.009 | 0.090 |
| 7134 | 0.007 | 0.005 | 0.006 | 0.238 |
| 7180 | 0.007 | 0.007 | 0.006 | 0.123 |
| 7193 | 0.006 | 0.005 | 0.007 | 0.084 |

… 
USE OF GLYCOSAMINOGLYCANS TO REDUCE NON-SPECIFIC BINDING IN IMMUNOASSAYS

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The invention relates to the field of immunoassays, and more particularly to the use of glycosaminoglycans to reduce non-specific binding in immunoassays.

BACKGROUND OF THE INVENTION

Biochemical binding assays are widely used to determine the presence and the concentration of analytes in biological specimens. Such assays are based on the concept of binding partners. An analyte of interest binds to an analyte binding agent (such as, for example, an antibody to the analyte, or a receptor for the analyte), and the analyte and the analyte binding agent are thus referred to as "binding partners". When one of the binding partners is bound to a solid phase, the assay is referred to as a heterogeneous assay. Such heterogeneous assays include, for example, the sandwich method, the indirect method, and the competitive method, all terms readily recognized in the art.

The sensitivity of an assay typically refers to the smallest mass of analyte that generates a statistically significant change in the signal generated by the assay when compared to the signal reading obtained in the absence of the analyte. Increased sensitivity is desirable because it permits detection of smaller amounts of analyte as well as an overall higher precision measurement of an analyte.

Non-specific binding refers to non-specific interactions of the binding partners in a heterogeneous assay system with a solid phase. Non-specific binding often reduces the sensitivity of heterogeneous assays, and it is therefore desirable to reduce such non-specific binding.

A number of methods are known for this purpose. For example, proteins, such as bovine serum albumin (BSA), gelatin, and casein, have been added to assay reagents or preadsorbed on the solid phase in order to block non-specific adsorption sites. Additionally, the use of various surfactants, often in high concentration, has been reported in the literature.

While these techniques may assist in reducing some non-specific adsorption, many of the techniques have been associated with interference with the desired specific interaction of the binding partners. These techniques may also lead to the displacement of the complex which is formed between the binding partners. Additionally, despite the use of high concentrations of protein and surfactant, a considerable amount of non-specific binding typically still exists in many heterogeneous assays. Alternative means to reduce non-specific binding in heterogeneous assays are thus needed.

This is especially true in the case of assays for cardiac troponin I where the levels of analyte being detected are very small and increased sensitivity is necessary for accurate and useful assay results. Cardiac Troponin I measurement aids in the accurate diagnosis of acute myocardial infarction and in the risk stratification of patients with non-ST-segment elevation acute coronary syndromes with respect to relative risk of mortality, myocardial infarction, or increased probability of ischemic events requiring urgent revascularization procedures.

Troponin I (TnI) is a protein normally found in muscle tissue that, in conjunction with Troponin T and Troponin C, regulates the calcium dependent interaction of actin and myosin (Tobacman, Annu Rev Physiol 58:447-481, 1996). Three isotypes of TnI have been identified: one associated with fast-twitch skeletal muscle, one with slow-twitch skeletal muscle, and one with cardiac muscle (Wilkinson and Grand, Nature 271:31-35, 1978; Bodor, J Clin Immunoassay 17(1): 40-44, 1994). The cardiac form has an additional 31 amino acid residues at the N-terminus and is the only troponin isoform present in the myocardium (Vallins et al., FEBS Letts 270(1,2):57-61, 1990) Clinical studies have demonstrated that cardiac troponin I (cTnI) is detectable in the bloodstream 4-6 hours after an acute myocardial infarct (AMI) and remains elevated for several days thereafter (Mair et al., Clin Chem 41(9):1266-1272, 1995; Larue et al., Clin Chem 39(6): 972-979, 1993). Thus, cTnI elevation covers the diagnostic windows of both creatine kinase-MB (CK-MB) and lactate dehydrogenase (Bodor, J Clin Immunoassay 17(1):40-44, 1994). Further studies have indicated that cTnI has a higher clinical specificity for myocardial injury than does CK-MB (Adams et al., Circulation 88(1):101-106, 1993; Apple et al., Clin Chim Acta 237:59-66, 1995).

Because of its cardiac specificity and sensitivity, cTnI has been used as a reliable marker in evaluating patients with unstable angina and non-ST segment elevation acute coronary syndrome (ACS). Previous clinical studies of patients with ACS (Lindahl et al., J Am Coll Cardiol 38:1497-1498, 2001; Venge et al., Am J Cardiol 89:1035-1041, 2002) have shown that minor increases in cTnI values provide important prognostic information about the short and long term risk of death (Galvani et al., Circulation 95:2053-2059, 1997; Antman et al., N Eng J Med 335:1342-1349, 1996; Ottani et al., Am Heart J40:917-927, 2000; Heidenreich et al., J Am Coll Cardiol 38:478-485, 2001). Ultimately, the assessment of the prognosis can be useful in identifying patients most likely to benefit from specific therapeutic interventions.

Thus, any reagents and methods for reducing non-specific binding in heterogeneous assays for cTnI, thus leading to increased sensitivity of cTnI assays, are desirable.

BRIEF SUMMARY OF THE INVENTION

To this end, the invention provides an immunoassay reagent which comprises an analyte binding agent in a diluent, and a glycosaminoglycan in an amount sufficient to reduce non-specific binding in an assay of a sample for the analyte.

In one presently preferred embodiment, the analyte is troponin, the analyte binding agent is an anti-troponin I monoclonal antibody, and the glycosaminoglycan is chondroitin sulfate.

Further provided is a sample composition which comprises a sample to be assayed for the presence of an analyte, an analyte binding agent, and a glycosaminoglycan other than heparin in an amount sufficient to reduce non-specific binding in an assay of the sample for the analyte.

In one presently preferred embodiment, the sample is serum or EDTA plasma, the analyte is troponin, the analyte binding agent is an anti-troponin I monoclonal antibody, and the glycosaminoglycan is chondroitin sulfate.

Also provided are methods of detecting an analyte in a sample, using a glycosaminoglycan to reduce non-specific binding in the method. The method comprises combining a sample to be analyzed for the presence of an analyte with a glycosaminoglycan and an analyte binding agent, so as to form a complex of any analyte present in the sample and the analyte binding agent, wherein the glycosaminoglycan reduces non-specific binding in the method, and detecting the resulting complex so as to detect the analyte. In the method, the preferred analyte is troponin, more preferably troponin I, and the preferred glycosaminoglycan is chondroitin sulfate.

Additional features and advantages of the subject invention will be apparent from the description which follows when considered in conjunction with the attached figures.

BRIEF DESCRIPTION OF THE DRAWINGS

FIG. 1 shows results of the TropI assay when various sugars were spiked into rogue TropI specimens;

FIG. 2 shows results of the TropI assay when BJ reagent was formulated with chondroitin sulfate at 0, 1, 2 and 4 mg/mL in the presence or absence of EDTA;

DETAILED DESCRIPTION OF THE INVENTION

Figures 3, 4:
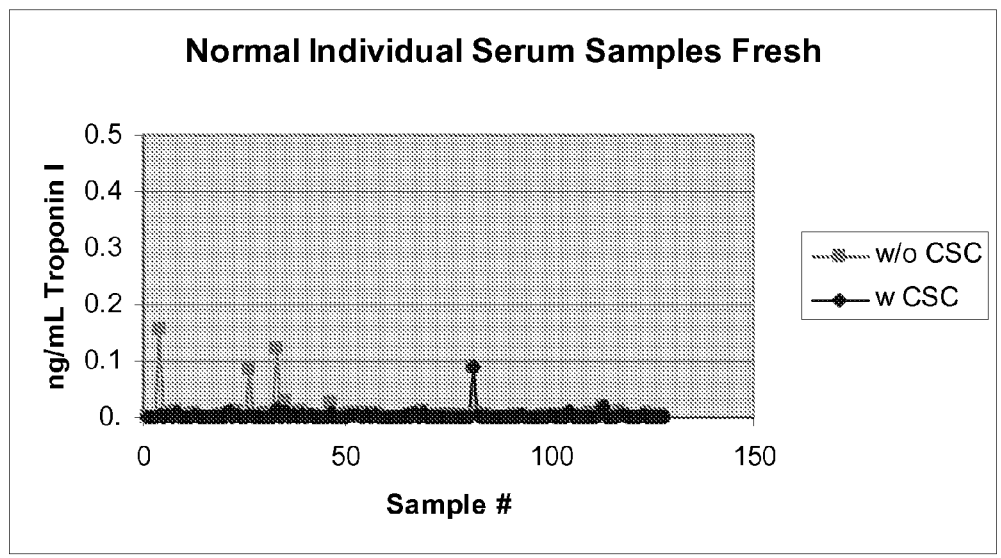
FIG. 3 shows results of the TropI assay with and without the addition of 0.5 mg/mL of CSC into the BJ reagent.
FIG. 4 shows results of the TropI assay when BJ reagent was formulated with various chondroitin sulfate isomers compared to Kit Lot (no chondroitin sulfate)
Figure 5:
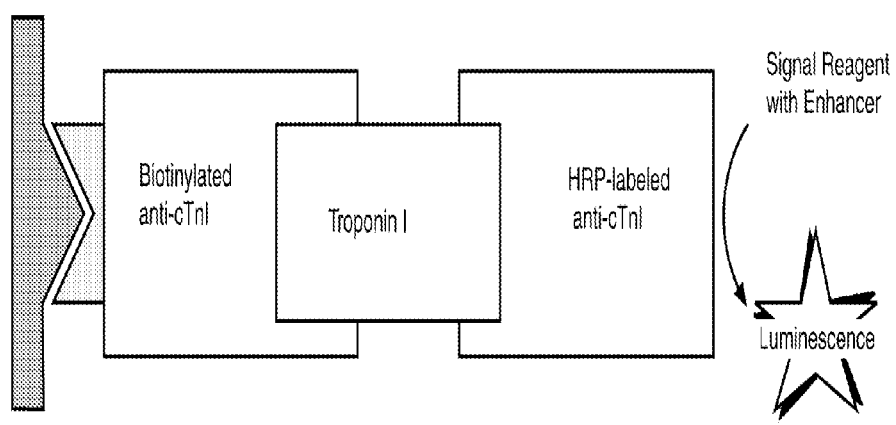
FIG. 5 illustrates the principles of the cardiac troponin I assay.

The invention provides an immunoassay reagent which comprises an analyte binding agent in a diluent, and a glycosaminoglycan in an amount sufficient to reduce non-specific binding in an assay of a sample for the analyte.

As discussed above, it is often desirable to determine the presence and the concentration of analytes in biological specimens. An analyte is a substance or chemical constituent that is determined in an analytical procedure (such as an immunoassay). Immunoassays are based on the concept of binding partners. An analyte of interest binds to an analyte binding agent (such as, for example, an antibody to the analyte, or a receptor for the analyte), and the analyte and the analyte binding agent are thus referred to as "binding partners".

In many immunoassays, the analyte binding agent is an antibody. Such antibodies are often provided in a diluent such as potassium phosphate buffer. The antibody may be of any immunoglobulin class, including, for example, IgG or IgM. The antibody may be a monoclonal antibody or a polyclonal antibody. In a sandwich type immunoassay, the analyte may be captured using an antibody or antibodies immobilized on a solid phase. Such immobilization can be accomplished using techniques known in the art, including the use of a streptavidin coated (SAC) solid phase, to which biotin labeled capture antibody or antibodies are bound. Analyte of interest present in a sample binds to the immobilized capture antibody or antibodies, and then labeled antibody or antibodies in turn bind to the captured analyte. The label may be any known in the art, and include, for example, horseradish peroxidase and alkaline phosphatase. Detected signal is then indicative of the amount of analyte present in the sample. The method of detection will depend upon the type of label chosen, as is known in the art, and could include calorimetric, fluorometric, or chemiluminescent methods.

The presently preferred glycosaminoglycan (GAG) is chondroitin sulfate, although other GAGs can also be used. These other GAGs include hyaluronate (also called hyaluronic acid), heparan sulfate, heparin, dermatan sulfate, and keratan sulfate. The chondroitin sulfate can be chondroitin sulfate A, chondroitin sulfate B (now referred to as dermatan sulfate), chondroitin sulfate C, or a mixture thereof.

Glycosaminoglycans (GAGs) or mucopolysaccharides are long unbranched polysaccharides containing a repeating disaccharide unit. The disaccharide units contain either of two modified sugars, N-acetylgalactosamine (GalNAc) or N-acetylglucosamine (GlcNAc), and a uronic acid such as glucuronate or iduronate. The hyaluronates are composed of D-glucuronate and GlcNAc. The dermatan sulfates are composed of D-glucuronic acid (GlcA) or L-iduronate (IdoA) and GalNAc-sulfate. Heterogeneity in dermatan sulfate results from varying degrees of O-sulfation and from the presence of the two uronic acids. Chondroitin sulfates are composed of D-glucuronate and GalNAc-6 (or 4)-sulfate. Heparin and heparan sulfates are composed of D-glucuronate-2-sulfate and N-sulfo-D-glucosamine-6-sulfate (heparans have less sulfate than heparins). Keratan sulfates are composed of galactose and galactose-6-sulfate and GlcNAc-6-sulfate.

Chondroitin sulfate (CS) is a sulfated glycosaminoglycan (GAG). A chondroitin chain can have over 100 individual sugars, each of which can be sulfated in variable positions and quantities. Chondroitin sulfate A refers to CS predominantly sulfated at carbon 4 of the GalNAc sugar (chondroitin-4-sulfate). Chondroitin sulfate B is now referred to as dermatan sulfate. Chondroitin sulfate C refers to CS predominantly sulfated at carbon 6 of the GalNAc sugar (chondroitin-6-sulfate). Chondroitin sulfate D refers to CS predominantly sulfated at carbon 2 of the GlcA and 6 of the GalNAc sugar (chondroitin-4,6-sulfate).

The glycosaminoglycan is provided in an amount sufficient to reduce non-specific binding in an assay of a sample for the analyte. When the GAG is chondroitin sulfate, the amount is preferably from about 0.25 mg/mL to about 4 mg/mL (equivalent to about 0.025% to about 0.4%). In one specific embodiment, the chondroitin sulfate is present in an amount of 1 mg/mL (equivalent to 0.1%). The examples which follow details of how to determine a suitable amount of GAG to utilize in accordance with the subject invention.

The sample to be analyzed for the presence of analyte can be any suitable sample, preferably a blood sample such as a serum sample or plasma sample. Blood plasma is the liquid component of blood in which the blood cells are suspended. A simple way to separate plasma from blood cells in a blood sample is by centrifugation. Serum refers to blood plasma in which clotting factors have been removed naturally by allowing the blood to clot prior to isolating the liquid component. Plasma samples are obtained from blood tubes which contain anticoagulants such as sodium heparin, sodium citrate, sodium fluoride, and potassium oxalate or potassium EDTA (ethylenediamine tetraacetic acid). In the case of a plasma sample in accordance with the subject invention, the plasma is preferably obtained using an anticoagulant other than heparin.

The immunoassay reagent of the subject invention, in one embodiment, comprises a monoclonal antibody specific for cardiac troponin I in a diluent, and 0.1% chondroitin sulfate. Suitable antibodies to cardiac troponin I are known in the art and particular pairs or combinations of antibodies are often recommended as assay partners. The antibodies of particular use herein are the monoclonal antibodies designated 19C7 and 24-40 as dual capture antibodies, labeled with biotin for attachment to a streptavidin coated well, and the antibody designated 16A11 as the detection antibody, labeled with horseradish peroxidase. These antibodies are commercially available (see sources referenced below) and are discussed throughout the literature in relation to assays for cardiac troponin I, and procedures for biotinylating and labeling are also well known in the art.

The above discussion refers to an immunoassay reagent which comprises the glycosaminoglycan in an amount sufficient to reduce non-specific binding. The GAG may be present in the diluent which contains the antibody.

Alternatively, the GAG may be added to a sample composition, to which the analyte binding agent is then added. The order of combination can vary, as long as the GAG is introduced prior to non-specific binding of any analyte present in the sample to the analyte binding agent.

Thus, further provided is a sample composition which comprises a sample to be assayed for the presence of an analyte, an analyte binding agent, and a glycosaminoglycan other than heparin in an amount sufficient to reduce non-specific binding in an assay of the sample for the analyte.

In one presently preferred embodiment, the sample is serum or EDTA plasma, the analyte is troponin, the analyte binding agent is an anti-troponin I monoclonal antibody, and the glycosaminoglycan is chondroitin sulfate.

Also provided is a method of detecting an analyte in a sample comprising: combining a sample to be analyzed for the presence of an analyte with a glycosaminoglycan and an analyte binding agent, so as to form a complex of any analyte present in the sample and the analyte binding agent, wherein the glycosaminoglycan reduces non-specific binding in the method; and detecting the resulting complex so as to detect the analyte. In one embodiment, the sample is combined with the glycosaminoglycan and the resulting sample is then combined with the analyte binding agent. In another embodiment, the sample is combined with the analyte binding agent and the resulting sample is then combined with the glycosaminoglycan. In yet another embodiment, the analyte binding agent is provided as an immunoassay reagent comprising the analyte binding agent in a diluent and the glycosaminoglycan, and the immunoassay reagent is combined with the sample. In each of these methods, the preferred analyte is troponin, more preferably troponin I, and the preferred glycosaminoglycan is chondroitin sulfate.

In the sample composition and methods according to the subject invention, the various suitable analyte binding agents, diluent, glycosaminoglycans, samples, and analytes are as discussed above in relation to the immunoassay reagent.

The reagents, compositions and methods of the subject invention are particularly useful in an immunoassay for cardiac troponin I. Further details of this embodiment are provided in the following examples.

Example I Effect of Adding Heparin to Cardiac Troponin I (cTnI or TropI) Assay Capture (BJ) and Detection (CJ) Reagents The objective of this experiment was to determine whether heparin addition to the TropI BJ and/or CJ reagents provides mitigation for false positive TropI results. Numerous reports of reproducible falsely elevated Troponin I results in serum samples were received. Several reports were also received of falsely elevated TropI results in EDTA plasma. In several instances, matching heparin plasma specimens obtained from the same patient did not show falsely elevated TropI results.

The experiment involved the spiking of heparin into the BJ and CJ reagents and the assay using these reagents was then run with rogue TropI samples that previously has been shown to give false positive TropI results.

The results show that heparin spiked into TropI CJ and run immediately was found to severely depress recovered signal. At only 10 units per mL of CJ the recovered Cal 2 (calibrator 2) signal was less than 50% of nominal. Heparin levels in heparin plasma in contrast are typically 25-50 units/mL. To give an equivalent concentration of heparin delivered by the CJ reagent would require heparin to be present at a level of 50-100 units/mL. Based on these responses, it is not feasible to add heparin to the CJ at levels that would be equivalent to heparinized plasma.

Using a panel of rogue serum specimens that had previously been identified as showing false positive TropI results, these were tested with CJ solution containing 10 units heparin per mL. These rogue specimens demonstrated significant reductions in the apparent cTnI (cardiac troponin I) concentration. Recovery ranged from 8-35% with specimens that untreated were found to have apparent cTnI concentrations of 0.7-7.0 ng/mL. None of these specimens however were completely corrected to below the Upper Reference Limit (URL) for serum.

The results of this experiment lead to the conclusions that heparin when added to the CJ formulation results in substantial reductions in the overall signal capacity for the reagents. At heparin concentrations of 10 units per mL, the signal was only 50% of nominal. Rogue patient specimens however were partially corrected by the addition of this level of heparin to the CJ. More complete correction of this interference, however, would require higher levels of heparin that would likely reduce the assay signal to levels incompatible with the assay design.

Example II Effect of Sugars as Sample Correction Factors in the BJ Reagent

The objective of this experiment was to assess the ability of sugars, such as those present in glycosaminoglycans and those typically associated with the carbohydrate side chains of horseradish peroxidase (HRP), to mitigate the effects of rogue TropI samples when added to the BJ reagents.

As discussed in Example I, heparin addition to rogue samples was shown to mitigate false positive results. Heparin is a member of a heterogeneous group of straight-chain anionic mucopolysaccharides, called glycosaminoglycans (GAGs), having anticoagulant properties. Although others may be present, the main sugars occurring in heparin are: $\alpha$-L-iduronic acid 2-sulfate; 2-deoxy-2-sulfamino-$\alpha$-D-glucose $\alpha$-sulfate; $\beta$-D-glucuronic acid; 2-acetamido-2-deoxy-$\alpha$-D-glucose; and $\alpha$-L-iduronic acid.

As an initial screening for possible sample correction factors, the following sugars were spiked into rogue TropI samples (to achieve a final concentration of 2 mg/mL of the test substance) to assess for effectiveness at blocking false positive reactions: N-acetyl-glucosamine (Sigma A8625); N-acetyl-galactosamine (Sigma A2795); glucosamine (Sigma G4875); N-acetylneuraminic acid (NANA, sialic acid) (Sigma A0812); chondroitin sulfate C (Sigma C4384); chitin (homopolymer of N-acetyl-glucosamine)(Sigma C9752); mucin (polymer of NANA)(Sigma M3895); and mannose (Sigma M8296). Chondroitin sulfate C(CSC) in this initial screening was found to significantly mitigate the false positive results (see FIG. 1). Apparent TropI results were generally suppressed to below the URL in all but one of the rogue samples. This latter sample is believed to be positive for heterophilic antibodies.

Based on these initial screening studies, follow-up experiments were conducted in which chondroitin sulfate C(CSC) was added directly to the BJ reagent at a series of increasing levels (0.25, 0.5, 1, 2, 3 and 4 mg/ml), with and without EDTA (5.58 mg/mL) in the BJ reagent (see FIGS. 2 and 3). Effectiveness of the formulations was based on blocking of the TropI rogue samples in conjunction with an assessment of the change in the reference calibrator responses. The lowest concentration of CSC that appears to effectively suppress the rogue TropI samples was 0.25 mg/mL; at slightly higher CSC levels (0.5 mg/mL) there appears to be a slight incremental improvement in blocking. The effect due to the presence or absence of EDTA with the additional reagent additives was not significant.

The addition of CSC at 0.25-0.5 mg/mL to the BJ formulation had little significant effect on the negative or positive serum pool controls. In addition, reference calibrator responses demonstrated little change to low levels for CSC. At CSC levels greater than 1 mg/mL, there was typically a 10-30% reduction in responses.

The results of this experiment lead to the conclusion that chondroitin sulfate C is an effective blocking agent to mitigate the non-specific background reactions (non-specific binding) that some serum and EDTA plasma specimens were found to demonstrate. While the lowest test level (0.25 mg/mL) demonstrated significant reductions in the apparent false positive reactions, slightly higher levels (0.5 mg/mL) may provide an additional measure of security for samples that may contain higher levels of the interferent. EDTA level in the presence of CSC did not appear to have a significant effect on the rogue samples.

CSC additions to the BJ reagent were observed to have minimal deleterious impact on the overall dose-response relationship when using the TropI reference calibrators. Across all eight reference calibrators, the changes induced by concentrations of CSC up to 1 mg/mL were generally less than 10%. Therefore, the addition of CSC to the BJ formulation at concentrations of 0.25-0.50 mg/mL would be expected to have little to no significant impact on the reference calibration.

Example III Rogue Samples with 0.05% CSC in BJ

The objective of this experiment was to test rogue samples using 0.5 mg/mL (0.05%) CSC in the BJ. The rogue samples predicted positive without the addition of CSC and negative with the 0.05% CSC added to the biotin diluent. The addition of 0.05% CSC appears to have no effect on the prediction of positive and negative samples. These results are shown in FIG. 3.

Example IV Comparative Performance of Chondroitin A, B and C

The objective of this experiment was to determine if any isomer of chondroitin sulfate would offer protection from rogue samples. The chondroitin sulfate C that is used in the above experiments is a mixture of chondroitin sulfate C with some chondroitin sulfate A. The lowest amount of chondroitin sulfate C in the mixture is 85%. Since there can be up to 15% of the A isomer, the A, B and C isomers were tested for efficacy.

The results obtained showed that all isomers of chondroitin sulfate were successful at reducing the observed concentration of the rogue samples, and there was no significant difference between the isomers in regard to the false positive suppression (see FIG. 4). This leads to the conclusion that the percent purity of the chondroitin sulfate in so far as the concentration of isomers A and B has no affect on the false positive suppression.

Example V the Cardiac Troponin I Assay

An immunometric immunoassay technique is used (see FIG. 5), which involves the simultaneous reaction of cardiac troponin I present in the sample with biotinylated antibodies (mouse monoclonal anti-cTnI: clone 19C7 which recognizes amino acids 41-49 of Troponin I and a second clone specific to the region of Troponin I comprising amino acids 24-40) and a horseradish peroxidase (HRP)-labeled antibody conjugate (mouse monoclonal anti-cTnI: clone 16A11 which recognizes amino acids 87-91 of Troponin I). The biotinylated-troponin Mabs react specifically with troponin I in a sample to form a complex that binds to streptavidin of a SAC well. Unbound materials are removed by washing and the troponin complex is detected using the HRP labeled Mab (which specifically binds to an epitope of troponin I that differs from the epitope to which the biotinylated Mabs bind). The bound HRP conjugate is measured by a luminescent reaction. A reagent containing luminogenic substrates (a luminol derivative and a peracid salt) and an electron transfer agent, is added to the wells. The HRP in the bound conjugates catalyzes the oxidation of the luminol derivative, producing light. The electron transfer agent (a substituted acetanilide) increases the level of light produced and prolongs its emission. The light signals are read by the VITROS™ Immunodiagnostic System (Ortho-Clinical Diagnostics, Inc., Raritan, N.J.). The amount of HRP conjugate bound is directly proportional to the concentration of cTnI present.

The assay protocol is as follows: 1) To a SAC well is added: 80 μL sample, 35 μL Biotin Reagent (BJ), and 35 μL Conjugate Reagent (CJ); 2) Incubate for 10 minutes 40 seconds; 3) Wash the SAC well; 4) Add 200 μL Signal Reagent and measure light emission.

The SAC wells are produced by coating polystyrene wells with streptavidin. Briefly, the polystyrene wells are first irradiated to 3.5 MRad to optimize adsorption of proteins. Biotinylated bovine serum albumin (B-BSA), produced by chemically coupling the biotin to the BSA using a commercially available activated ester (biotin-XX-NHS, Calbiochem, Nottingham, UK) is coated onto the polystyrene wells. The coating is carried out by incubating the wells with the B-BSA solution for 10 minutes. The B-BSA is physically adsorbed and not covalently bound to the polystyrene surface. The wells are washed before overcoating with streptavidin. Streptavidin is coated onto the wells by incubating a streptavidin solution with the biotin covered surface for 50 minutes. The interaction between streptavidin and biotin is non-covalent, but exceptionally strong ($10^{15}$ L/mol). The wells are washed again before drying and storing.

Streptavidin has four binding sites for biotin and so after immobilization of the streptavidin on the surface there are free biotin binding sites. These binding sites are available to react with biotinylated components of the assay.

The Conjugate Reagent (CJ) comprises the following components:

| Component | Amount g/L |
|---|---|
| Water | 849.3 |
| $K_2HPO_4$ | 13 |
| $KH_2PO_4$ | 17 |
| Kathon | 20 |
| BSA 30% | 100 |
| HRP labeled mab 16A11 clone | 4 mg/L |
| pH | 6.6 |

The Assay or Capture Reagent (BJ) comprises the following components:

| Component | Amount g/L | |
|---|---|---|
| Water | | |
| K$_2$HPO$_4$ | 13 | |
| KH$_2$PO$_4$ | 17 | |
| Kathon | 20 | |
| Bovine Serum Albumin 30% | 100 | |
| EDTA (equimolar disodium and trisodium) | 15 | mM |
| Chondroitin Sulfate C | 1 | |
| Biotinylated mab 24-40aa specific clone | 5.5 | mg/L |
| Biotinylated mab 19C7 clone | 3 | mg/L |
| pH | 6.6 | |

The Monoclonal Antibodies are available commercially. HyTest, Ltd (Itainen Pitkakatu 4C, Pharma City, Torku, Finland 20520) is a supplier of mouse monoclonal antibody clone 19C7, specific to the region of troponin I comprising amino acids 41-49. This Mab is biotinylated as provided below. HyTest is also a supplier of mouse monoclonal antibody clone 16A11, specific to the region of troponin I comprising amino acids 87-91. This Mab is labeled with HRP as provided below. Strategic BioSolutions (111 Pencader Dr., Newark, Del., USA 19702) is a supplier of a mouse monoclonal antibody clone specific to the region of troponin I comprising amino acids 24-40. This Mab is biotinylated as below.

The biotinylation procedure involves the following: The 19C7 clone and the Strategic BioSolutions 24-40 directed clone are conjugated to biotin individually using well known region-specific chemistry.

The HRP labeling procedure involves the following: The 16A11 clone from HyTest is conjugated to HRP using the following methodology: 1) The Mab is activated with maleimide groups by reacting it with sulfo-SMCC [sulfosuccinimidyl 4-(N-maleimidomethyl)cyclohexane-1-carboxylate]; 2) The HRP is activated with thiol groups by reacting it with NHS-SATA [s-acetyl thioacetic acid N-hydroxysuccinimide]; 3) Both activated reagents are purified and then reacted together to produce the 16A11-HRP, which is then purified.

While particular embodiments of the invention have been shown, it will be understood, of course, that the invention is not limited thereto, since modifications may be made by those skilled in the art, particularly in light of the foregoing teachings. Reasonable variation and modification are possible within the scope of the foregoing disclosure of the invention without departing from the spirit of the invention.

The invention claimed is:

1. An immunoassay reagent comprising: a troponin I binding agent in a diluent; and chondroitin sulfate in an amount sufficient to reduce non-specific binding in an assay of a sample for the troponin I, wherein the chondroitin sulfate is present in an amount from about 0.25 mg/mL to about 4 mg/mL.

2. The immunoassay reagent of claim 1 wherein the chondroitin sulfate is present in an amount of about 1 mg/mL.

3. The immunoassay reagent of claim 1 wherein the troponin I binding agent is an antibody.

4. A sample composition comprising:
a sample to be assayed for the presence of troponin I; and
the immunoassay reagent of claim 1.

5. The sample composition of claim 4 wherein the sample is a serum sample.

6. The sample composition of claim 4 wherein the sample is a plasma sample containing ethylenediamine tetraacetic acid.

7. The sample composition of claim 4 wherein the troponin I binding agent is an antibody.

8. A method of detecting troponin I in a sample, the method comprising:
combining a sample to be assayed for the presence of troponin I with the immunoassay reagent of claim 1, so as to form a complex of any troponin I present in the sample and the troponin I binding agent, wherein the chondroitin sulfate reduces non-specific binding in the method; and
detecting the resulting complex so as to detect the troponin I.

* * * * *